US005473933A

United States Patent [19]
Soga et al.

[11] Patent Number: 5,473,933
[45] Date of Patent: * Dec. 12, 1995

[54] HUMIDITY SENSOR

[75] Inventors: Mamoru Soga, Osaka; Shinji Ozaki, Yao; Shigeo Ikuta, Tondabayashi; Kazufumi Ogawa, Hirakata, all of Japan

[73] Assignee: Matsushita Electric Industrial Co., Ltd., Osaka, Japan

[*] Notice: The portion of the term of this patent subsequent to Feb. 16, 2000, has been disclaimed.

[21] Appl. No.: 287,590

[22] Filed: Aug. 8, 1994

Related U.S. Application Data

[63] Continuation of Ser. No. 37,422, Mar. 26, 1993, abandoned.

[30]  Foreign Application Priority Data

Apr. 24, 1992 [JP] Japan .................................. 4-107069

[51] Int. Cl.[6] .................................................. G01N 33/18
[52] U.S. Cl. .......................................... 73/29.2; 73/335.04
[58] Field of Search ............................. 73/29.01, 29.02, 73/335.04, 335.05; 252/572, 963

[56]  References Cited

U.S. PATENT DOCUMENTS

| | | | |
|---|---|---|---|
| 3,168,829 | 2/1965 | Nelson | 73/335.05 |
| 4,166,891 | 9/1974 | Elliot | 525/329 |
| 4,373,392 | 2/1983 | Nagamoto | 73/335.05 |
| 4,843,517 | 6/1989 | Maruyama et al. | 252/573 |
| 4,954,694 | 9/1990 | Nagai et al. | 219/413 |
| 5,036,704 | 8/1991 | Pusatcioglu et al. | 73/335.02 |
| 5,045,828 | 9/1991 | Kulwicki et al. | 338/35 |
| 5,069,069 | 12/1991 | Miyagishi et al. | 73/335.01 |
| 5,079,407 | 1/1992 | Baker | 219/448 |
| 5,103,371 | 4/1992 | Ogawa et al. | 361/323 |
| 5,187,639 | 2/1993 | Ogawa et al. | 361/323 |
| 5,234,718 | 8/1993 | Mino et al. | 427/352 |

FOREIGN PATENT DOCUMENTS

| | | |
|---|---|---|
| 0076131 | 4/1983 | European Pat. Off. . |
| 0372697 | 6/1990 | European Pat. Off. . |
| 0102150 | 6/1984 | Japan . |
| 0102149 | 6/1984 | Japan . |
| 0090039 | 11/1984 | Japan . |
| 62-245149 | 10/1987 | Japan . |

OTHER PUBLICATIONS

Patent Abstract of Japan, vol. 8, No. 204—JP-A-59 090 039 (May 24, 1984).
Patent Abstract of Japan, vol. 15, No. 410—JP-A-31 065 247 (Jul. 17, 1991).

Primary Examiner—Timothy M. McMahon
Assistant Examiner—Robert Carpenter
Attorney, Agent, or Firm—Fish & Richardson

[57]  ABSTRACT

A humidity sensor with an excellent water-repelling property is presented by covalently bonding a monomolecular film containing fluoroalkyl groups to the surface of a humidity sensing element, used for the sensor, via siloxane bonding. A chemically adsorbed monomolecular film containing fluoroalkyl groups is formed on the surface of a humidity sensing element via siloxane bonding after dipping and holding the element in a surface active solution such as heptadecafluorotridecyl trichlorosilane, and removing the unreacted material.

7 Claims, 4 Drawing Sheets

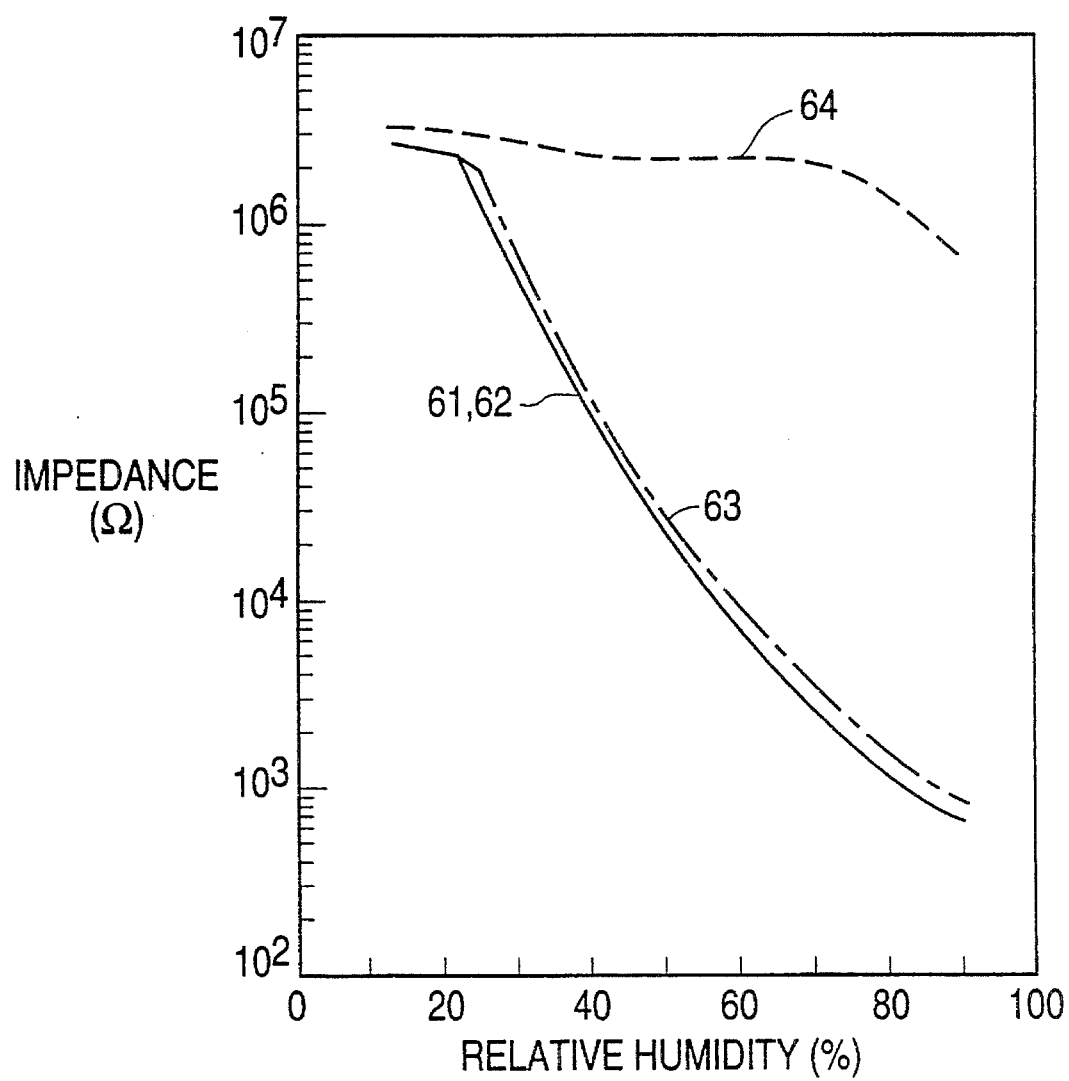

HUMIDITY SENSOR

This application is a continuation of U.S. application Ser. No. 08/037,422, filed Mar. 26, 1993, now abandoned.

FIELD OF THE INVENTION

The invention relates to a humidity sensor; more particularly, the invention relates to a humidity sensor with improved water-repelling properties.

BACKGROUND OF THE INVENTION

Humidity sensors have been utilized for controlling the humidity of air-conditioning and heating elements, and detecting the vapor of desiccators and automatic cooking appliances such as ovens and microwaves.

For methods of detecting humidity, a variety of physical and chemical phenomena has been employed. For detecting humidity using an electrical signal, however, methods of sensing the changes in the electric capacitance or the resistance of ceramics and organic macromolecules are generally known. A ceramic humidity sensor employing porous ceramics for a humidity sensing element and a polymer humidity sensor are also well known.

However, the above-noted humidity sensors can be used only in limited environments; in the case of using the sensors in a moist environment, drops of water may stick to a humidity sensing element or the material of the element, polyelectrolyte, thus causing it to melt and thereby degrading characteristics of such sensors.

SUMMARY OF THE INVENTION

An objective of the invention is to provide a humidity sensor with an excellent water-repelling property, thus solving the above-noted problems.

In order to accomplish this objective, the surface of a humidity sensing element used in a humidity sensor according to the invention or its casing, housing the humidity sensing element, is coated with a chemically adsorbed film containing molecules possessing fluorocarbon groups bonded via —Si— covalent bonding, and trifluoro groups are arranged in an outer layer of the film.

In the above-noted composition, it is preferable that the sensor comprises an inorganic siloxane inner layer between the surface of the humidity sensing element or the casing and at least one organic group, and that the surface, the inner layer and the organic group are covalently bonded with each other.

In the above-noted composition, it is preferable that a chemically adsorbed film is monomolecular film, polymer film or an accumulation of a plurality of monomolecular films.

In the above-noted composition, it is preferable that the humidity sensing element is at least one material selected from magnesium spinel rutile, $ZrO_2$ and $MgO$, and these materials impregnated with a polyelectrolyte.

It is preferable that the resin used for the casing is at least one material selected from polybutyleneterephthalate and nylon/ABS composition.

The humidity sensing element used for the humidity sensor of the invention has excellent water-repelling properties since its surface is coated with a chemically adsorbed film containing fluoroalkyl groups bonded via siloxane groups to the surface of the sensor. Because of this film, water drops do not stick to the element even when it gets wet with dew or water. Based on the fact that the base of the chemically adsorbed film is formed by chemical bonding via a siloxane bond, a film excellent in durability is formed. Because the chemically adsorbed film of the invention is an ultrathin film with a thickness at the nanometer or angstrom level, it does not degrade the characteristics of the sensor.

The casing used for the humidity sensor of the invention has its surface coated with a chemically adsorbed film possessing fluoroalkyl groups bonded to the surface via a siloxane bond. Because of this film, water drops do not penetrate the casing and adhere to a humidity sensing element even if the casing becomes wet with dew or water. In addition, based on the fact that the base of the chemically adsorbed film is formed by chemical bonding via siloxane groups, a film excellent in durability is formed.

In a preferred embodiment of the invention in which the chemically adsorbed film is a monomolecular or polymer film, a film with a uniform thickness and excellent water-repelling properties can be formed.

BRIEF DESCRIPTION OF THE DRAWINGS

FIG. 6 is a graph comparing characteristics of the humidity sensors of Examples 7 to 10 and Reference 2 before and after water resistance tests.

DETAILED DESCRIPTION OF THE INVENTION

The invention is described by referring to the figures.

Figure 1:
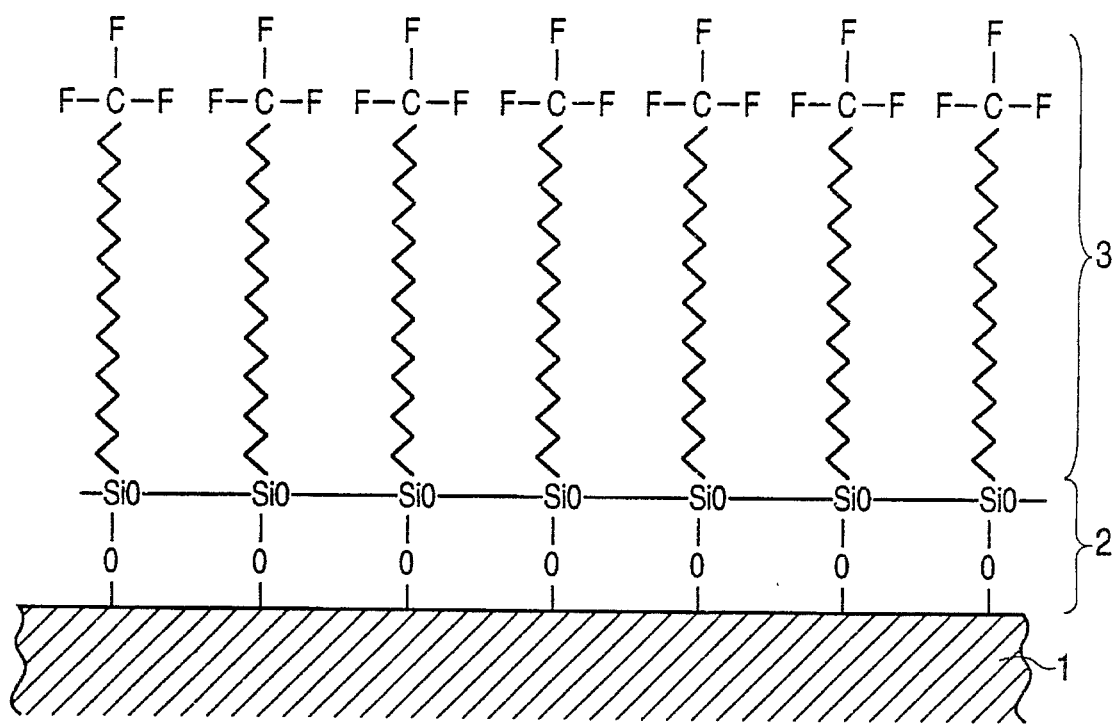
FIG. 1 is a cross-sectional conceptional diagram, magnified to a molecular level, showing the surface of a humidity sensing element used for a humidity sensor of this invention.

As shown in FIG. 1, the humidity sensor of Example 1 of the invention comprises a humidity sensing elemement 1 with its surface coated with a monomolecular film 3 possessing fluoroalkyl groups bonded to the surface via siloxane bond groups 2.

Figure 3:
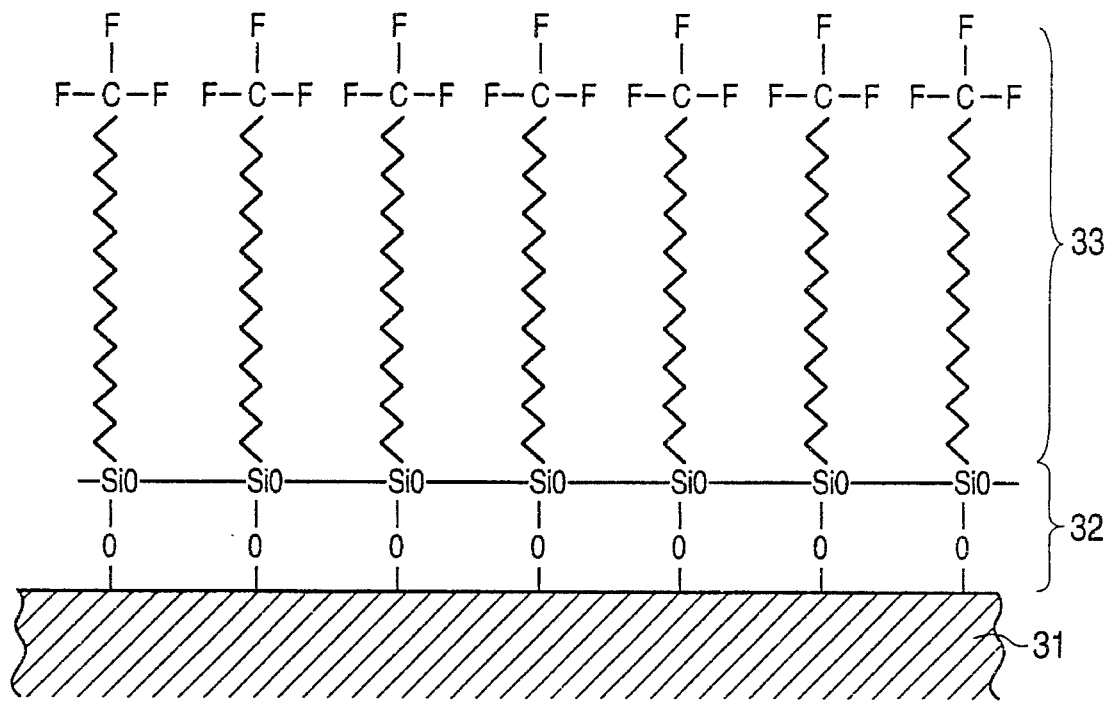
FIG. 3 is a cross-sectional conceptional diagram, magnified to a molecular level, showing the surface of a casing used for a humidity sensor according to this invention.

As shown in FIG. 3, the humidity sensor of Example 2 of the invention comprises a casing 31 with its surface coated with a monomolecular film 33 possessing fluoroalkyl groups bonded to the surface via siloxane bond groups 32.

As materials for the humidity sensing element, porous ceramics such as magnesium spinel ($MgCiO_4$), rutile ($TiO_2$), materials made of $ZrO_2$ and $MgO$, and these materials impregnated with polyelectrolyte, are commonly used. For macromolecules, hydrophilic quarternary ammonium salt resin (a thermoserring resin) crosslinked with hydrophobic melamine resin (a thermoserring resin) is frequently applied.

As resin materials used for the casing of the invention, polybutyleneterephthalate, nylon/ABS compound or the like are used.

A chemically adsorbed film formed on the surface of a humidity sensing element or a casing is composed of a chlorosilane-based surface active agent possessing fluorocarbon groups. Trichlorosilane-, monochlorosilane- and dichlorosilane-based surface active agents mentioned below are examples of chlorosilane-based active agents possessing fluorocarbon groups.

Trichlorosilane-based active agents include the following examples:

$CF_3(CF_2)_7(CH_2)_2SiCl_3$;
$CF_3CH_2O(CH_2)_{15}SiCl_3$;
$CF_3(CH_2)_2Si(CH_3)_2(CH_2)_{15}SiCl_3$;
$F(CF_2)_4(CH_2)_2Si(CH_3)_2(CH_2)_9SiCl_3$;
$F(CF_2)_8(CH_2)_2Si(CH_3)_2(CH_2)_9SiCl_3$;
$F(CF_2)_8(CH_2)_2Si(CH_3)_2(CH_2)_{10}SiCl_3$;
$CF_3COO(CH_2)_{15}SiCl_3$;
$CF_3(CF_2)_5(CH_2)_2SiCl_3$

Monochlorosilane- or dichlorosilane-based surface active agents with lower-alkyl groups substituted are shown in the following examples:

$CF_3(CF_2)_7(CH_2)_2SiCl_n(CH_3)_{3-n}$;
$CF_3(CF_2)_7(CH_2)_2SiCl_n(C_2H_5)_{3-n}$;
$CF_3CH_2O(CH_2)_{15}SiCl_n(CH_3)_{3-n}$;
$CF_3CH_2O(CH_2)_{15}SiCl_n(C_2H_5)_{3-n}$;
$CF_3(CH_2)_2Si(CH_3)_2(CH_2)_{15}SiCl_n(CH_3)_{3-n}$;
$F(CF_2)_4(CH_2)_2Si(CH_3)_2(CH_2)_9SiCl_n(C_2H_5)_{3-n}$;
$F(CF_2)_8(CH_2)_2Si(CH_3)_2(CH_2)_9SiCl_n(CH_3)_{3-n}$;
$CF_3COO(CH_2)_{15}SiCl_n(CH_3)_{3-n}$;
$CF_3(CF_2)_5(CH_2)_2SiCl_n(CH_3)_{3-n}$ where n represents 1 or 2.

Among these examples, trichlorosilane-based surface active agents are preferred in that chlorosilyl bonds other than those bonded to their hydrophilic groups form intermolecular bonds with adjacent chlorosilane groups via a siloxane bond, thereby permitting the formation of a more firmly adsorbed film. Furthermore, $CF_3(CF_2)_nCH_2CH_2SiCl_3$ (wherein n is an integer, most suitably 3 to 25) is preferred because of its balanced solvent solubility, chemical adsorption and anti-contamination properties. In incorporating a vinylene group (—C=C—) or an acetylenic (ethynyl) group in the fluoroalkyl chain portion, the formed chemically adsorbed film can be crosslinked by being irradiated with an electron beam of about 5 Mrads, thus further improving the firmness of the chemically adsorbed film. The chlorosilane-based surface active agents capable of use according to the invention are not limited to those in the form of a straight chain as noted above. It is possible to use agents with branched fluoroalkyl or hydrocarbon groups or those with silicons at one end being substituted by fluoroalkyl or hydrocarbon groups (i.e. $R^2SiCl_2$, $R^3SiCl$, $R^1R^2SiCl_2$, $R^1R^2R^3SiCl$ or the like, where R, $R^1$, $R^2$ and $R^3$ represent fluoroalkyl or hydrocarbon group) To increase the adsorption density, however, the straight chain form is preferred.

Moreover, on the surface of a humidity sensing element or a casing used for a humidity sensor, an inorganic siloxane-based inner layer can be formed to increase hydrophilic groups.

The surface of a humidity sensing element or casing becomes hydrophilic by the following procedures:

chemically adsorbing to the surface of the element an agent with a plurality of chlorosilyl bonds, such as $SiCl_4$, $SiHCl_3$, $SiH_2Cl_2$, $Cl—(SiCl_2O)_n—SiCl_3$, $SiCl_m(CH_3)_{4-m}$, $SiCl_m(C_2H_5)_{4-m}$, $HSiCl_r(CH_3)_{3-r}$, $HSiCl_r(C_2H_5)_{3-r}$ or the like (n as a natural number; m as an integer from 1 or 3; r as 1 or 2);

reacting the adsorbed surface with water, thereby changing the chlorosilyl bonds on the surface to hydrophilic silanol bonds.

Among agents with a plurality of chlorosilyl groups, tetrachlorosilane ($SiCl_4$) is preferred in that it is highly reactive and low in molecular weight. Therefore, it can provide silanol bonds at high density. To the inner layer, a chlorosilane-based surface active agent containing fluoroalkyl groups may be chemically adsorbed. In this way, a chemically adsorbed film with an increased density can obtain improved water-repelling properties.

The method of forming a chemically adsorbed film containing fluoroalkyl groups on the surface of a humidity sensing element or a casing via a siloxane bond comprises the following procedures:

dipping and holding the sensing element or casing in a nonaqueous organic solvent;

chemically adsorbing on the element or casing a chlorosilane-based surface active agent, thereby forming a chemically adsorbed film containing fluoroalkyl groups on the surface via siloxane bond;

or alternatively, contacting the humidity sensing element or the casing with a halogenated silane-based chemical adsorbent in a gaseous phase;

reacting with water, thus forming a chemically adsorbed film on the surface of the sensing element or the casing.

The nonaqueous solvent used for the above-noted procedures may be any organic solvent so long as it does not have active hydrogen able to react with the chlorosilane-based surface active agent. Any of the solvents—including a fluorine-, hydrocarbon-, ether- and ester-based solvent—can be a preferable organic solvent.

Examples of fluorine-based solvents are as follows:

1,1-dichloro,1-fluoroethane;

1,1-dichloro,2,2,2-trifluoroethane;

1,1-dichloro-2,2,3,3,3-pentafluoropropane;

1,3-dichloro,1,1,2,2,3-heptafluoropropane;

trifluoroalkylamine;

perfluorofuran and its fluoroalkyl derivative.

Hydrocarbon-based solvents include the following:

hexane; octane; hexadecane; cyclohexane; etc.

Ether-based solvents include the following:

dibutylether; dibenzylether; etc.

Ester-based solvents include the following:

methyl acetate; ethyl acetate; isopropyl acetate; amyl acetate; etc.

Incidentally, the chemically adsorbed film formed on the surface of the humidity sensing element or the casing of the humidity sensor of the invention sufficiently exhibits its desired advantages with only one layer of a monomolecular chemically adsorbed film.

A single layer of a chemically adsorbed monomolecular film can be formed on the surface simply by following the procedures mentioned below:

chemically adsorbing on the element or casing an agent with a plurality of chlorosilyl groups or a chlorosilane-based surface active agent;

washing with a nonaqueous solvent without allowing the element or casing to come into contact with moisture.

The procedures are therefore done easily without any specialized procedure. Of course, the chemically adsorbed film may be formed by accumulating monomolecular films; in this way, the groups showing the added function are oriented and the density is enhanced, so that further benefits may be exhibited. The procedure of washing the surface with a nonaqueous solvent should be omitted when forming a chemically adsorbed polymer film of the invention.

The invention is further described below by referring to the following practical embodiments:

EXAMPLE 1

Figure 2:
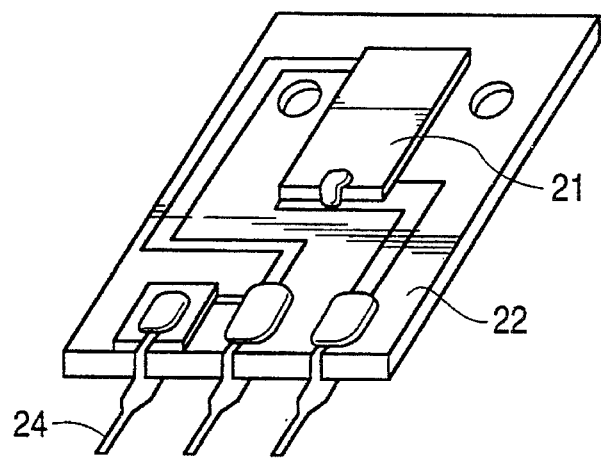
FIG. 2 is an example of a humidity sensing element used in a humidity sensor according to this invention.

The humidity sensor shown in FIG. 2 (wherein 21 is a humidity sensing element, 22 is an plate, and 24 is a lead) was made by impregnating a humidity sensing element composed of semiconductor porous ceramics, made with magnesium spinel and futile, with alkylamine epichlorohydrin as a polyelectrolyte.

A chemically adsorbed monomolecular film containing fluoroalkyl groups was formed on the surface of a humidity sensing element via siloxane bond by the following procedures:

dipping and holding the humidity sensor (FIG. 2) in a $10^{-2}$ mol/liter cyclohexane solution of heptadecafluorodecyl trichlorosilane for 120 minutes at room temperature in a nitrogen atmosphere;

washing the unreacted heptadecafluorodecyl trichlorosilane off the humidity sensor with cyclohexane, and then with pure water.

EXAMPLE 2

A chemically adsorbed monomolecular film containing fluoroalkyl groups was formed on the surface of a humidity sensing element via siloxane bond as follows:

dipping and holding the same humidity sensor as in Example 1 in a 1% by weight of tetrachlorosilane solution [solvent: tri(n-nonafluorobutyl)amine] for 60 minutes at room temperature in a nitrogen atmosphere;

washing the unreacted tetrachlorosilane off the sensor with tri(n-nonafluorobutyl)amine, and then with pure water;

dipping and holding the dried sensor in tri(n-nonafluorobutyl)amine solution by using heptadecafluorodecyl trichlorosilane at a concentration of $10^{-2}$ mol/liter as the chlorosilane-based surface active agent containing fluoroalkyl groups, for 120 minutes at room temperature in a nitrogen atmosphere;

washing the unreacted heptadecafluorodecyl trichlorosilane off the sensor with tri(n-nonafluorobutyl)amine, and then with pure water.

EXAMPLE 3

An experiment similar to Example 1 was conducted in this example, except that heptadecafluorodecyl trichlorosilane was replaced with 9-(heptadecafluorodecyl dimethylsilyl) nonyltrichlorosilane.

EXAMPLE 4

An experiment similar to Example 2 was conducted in this example, except that tetrachlorosilane was replaced with hexachlorodisiloxane.

EXAMPLE 5

The humidity sensing element in Example 1 was exposed to vaporized heptadecafluorodecyl trichlorosilane (used as a chlorosilane-based surface active agent containing fluoroalkyl groups) in a desiccator for 120 minutes, thus forming a chemically adsorbed monomolecular film containing fluoroalkyl groups on the surface of the sensing element via siloxane bonds. The sensing element was then left in an air atmosphere for 60 minutes; as a result, siloxane bonds were formed between admolecules.

EXAMPLE 6

The steps of Example 5 were conducted in this example by following the procedure of leaving a humidity sensing element in vaporized hexachlorodisiloxane for 60 minutes and then in an air atmosphere for another 60 minutes.

Reference 1

An experiment similar to Example 1 was conducted in this example, except that the humidity sensor of Example 1 was replaced with a sensor lacking the formation of a chemically adsorbed film.

EXAMPLE 7

Figure 4:
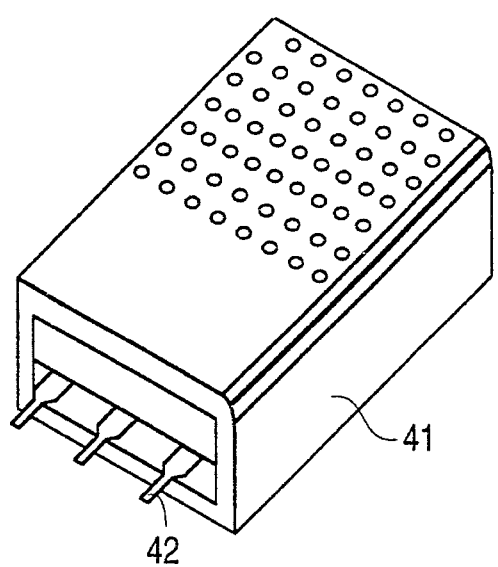
FIG. 4 is an example of a package used for a humidity sensor of the invention.

A chemically adsorbed monomolecular film containing fluoroalkyl groups was formed on the surface of a casing via siloxane bonds by the following procedures:

treating the casing shown in FIG. 4, (wherein 41 is a casing and 42 is a lead) made of polybutyleneterephthalete, with oxygen plasma at an oxygen flow rate of 1 liter/minute in UV dry stripper (UV-1, made by SAMCO International) for 10 minutes;

dipping and holding the casing in a cyclohexane solution, in which heptadecafluorodecyl trichlorosilane at a concentration of $10^{-2}$ mol/liter was dissolved, for 120 minutes at room temperature in a nitrogen atmosphere;

washing the casing with pure water, thereby forming a chemically adsorbed monomolecular film on its surface.

The sensor in Reference 1 was then inserted into this casing.

EXAMPLE 8

A chemically adsorbed monomolecular film containing fluoroalkyl groups was formed on a casing surface via siloxane bonds as follows:

dipping and holding the casing as in Example 7 in 1% by weight of tetrachlorosilane solution [solvent: tri(n-nonafluorobutyl)amine] for 60 minutes at room temperature in a nitrogen atmosphere;

washing the casing with pure water;

dipping and holding the dried casing in tri(n-nonafluorobutyl)amine solution by using heptadecafluorodecyl trichlorosilane, at a concentration of $10^{-2}$ mol/liter as a chlorosilane-based surface active agent containing fluoroalkyl groups, for 120 minutes at room temperature in a nitrogen atmosphere;

washing the unreacted heptadecafluorodecyl trichlorosilane with tri(n-nonafluorobutyl)amine solvent, and then with pure water, thus forming a chemically adsorbed monomolecular film on the casing surface.

The humidity sensor of Reference 1 was inserted into this casing.

EXAMPLE 9

An experiment similar to Example 7 was conducted in this example, except that heptadecafluorodecyl trichlorosilane was replaced with 9-(heptadecafluorodecyl dimethylsilyl ) nonyltrichlorosilane.

EXAMPLE 10

An experiment similar to Example 8 was conducted in this example, except that tetrachlorosilane was replaced with hexachlorodisiloxane.

Reference 2

The humidity sensor of Reference 1 was inserted into the casing of Example 7 without the adsorbed film.

As a water resistance test, 100 repetitions of the procedures of dipping and holding in water for one hour, and drying with a wind of 3 m/second for 90 seconds were performed on the humidity sensors of Examples 1 to 6, Reference 1, Examples 7 to 10 and Reference 2. Impedances before and after the test were measured at 25° C. and with AC 1V, and with a sine wave in the range of 10%–90% relative humidity; the results are shown in FIGS. 5 and 6.

Figure 5:
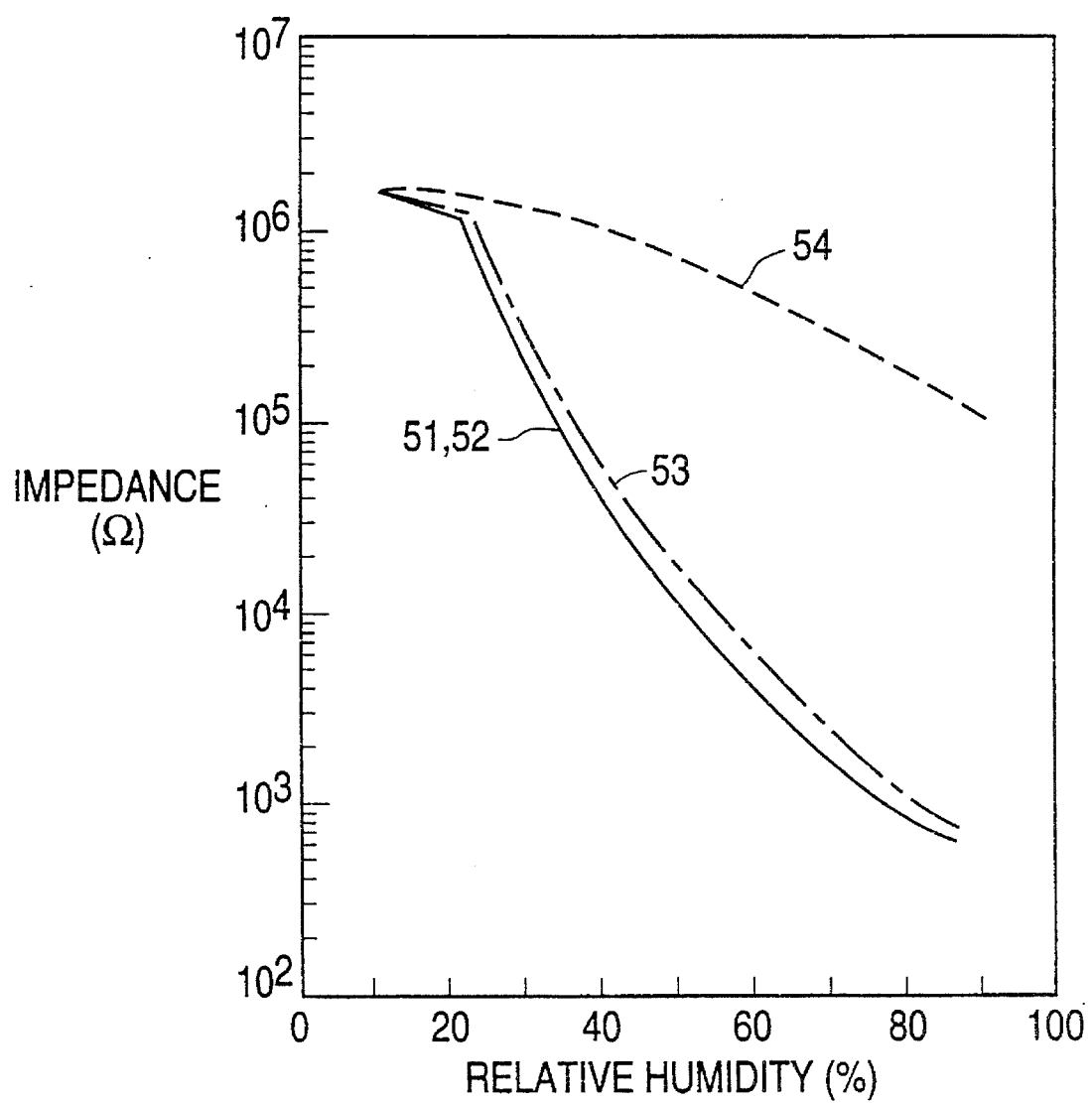
FIG. 5 is a graph comparing characteristics of the humidity sensors of Examples 1 to 6 and Reference 1 before and after water resistance tests.

FIG. 5 shows the test results of Examples 1 to 6 and Reference 1 while FIG. 6 shows the results of Examples 7 to 10 and Reference 2.

In FIG. 5, numerals 51 shows the impedance of the humidity sensors of Examples 1–6 before the water resistance tests; 52 shows the impedance of the humidity sensors of Reference 1 before the test; 53 shows the impedance of the humidity sensors of Examples 1–6 after the tests; 54 shows the impedance of the humidity sensors of Reference 1 after the test.

In FIG. 6, numerals 61 shows the impedance of the humidity sensors of Examples 7–10 before the tests; 62 shows the impedance of the humidity sensors of Reference 2 before the test; 63 shows the impedance of the humidity sensors of Examples 7–10 after the tests; and 64 shows the impedance of the humidity sensors of Reference 2 after the test.

As seen from FIGS. 5 and 6, the values obtained from the humidity sensors of the invention after the test were nearly the same as the ones obtained before the test. However, the values of the sensors in the References were significantly changed after the test, showing a lack of functional properties as a humidity sensor.

As explained in the above-noted examples, the humidity sensor of the invention comprises a humidity sensing element and/or a casing with its surface coated with a chemically adsorbed film containing fluoroalkyl groups bonded to the surface through siloxane bond; therefore, the sensor has excellent water-repelling properties compared with the prior art. As a result, even if the sensor is used continuously under a moisture-laden environment, it does not lose its functional properties as a humidity sensor.

The invention may be embodied in other specific forms without departing from the spirit or essential characteristics thereof. The embodiments disclosed in this application are to be considered in all respects as illustrative and not restrictive, the scope of the invention being indicated by the appended claims rather than by the foregoing description, and all changes which come within the meaning and range of equivalency of the claims are intended to be embraced therein.

We claim:

1. A humidity sensor comprising: a chemically adsorbed film comprising molecules possessing fluorocarbon groups, said film bonded to a surface of a humidity sensing element or a casing used for housing said humidity sensing element via—Si— covalent bonding, wherein trifluoro groups are arranged in an outer layer of said chemically adsorbed film, and wherein said surface is coated with said chemically adsorbed film.

2. The humidity sensor according to claim 1 comprising an inorganic siloxane inner layer between said film and said surface of the humidity sensing element or the casing, said humidity sensing element surface being covalently bonded to said inner layer, and said inner layer being covalently bonded to said at least one organic group.

3. The humidity sensor as in one of claim 1 or 2, wherein said chemically adsorbed film is a monomolecular film, polymer film or an accumulation of a plurality of monomolecular films.

4. The humidity sensor according to claim 1, wherein said humidity sensing element comprises at least one material selected from the group consisting of magnesium spinel, rutile zirconium oxide and magnesium oxide.

5. The humidity sensor according to claim 4, wherein said material is impregnated with polyelectrolyte.

6. The humidity sensor according to claim 1, wherein a resin used for said casing is at least one material chosen from the group consisting of polybutyleneterephthalete and nylon/ABS compositions.

7. The humidity sensor as in claim 1, wherein the molecules possessing fluorocarbon groups contains chlorosilane groups.

* * * * *

UNITED STATES PATENT AND TRADEMARK OFFICE
CERTIFICATE OF CORRECTION

PATENT NO. : 5,473,933
DATED : December 12, 1995
INVENTOR(S) : Mamoru SOGA, Shinji OZAKI, Shigeo IKUTA It is certified that error appears in the above-indentified patent and that said Letters Patent is hereby corrected as shown below:

On the Title page, item [*] Notice should be changed to read --

June 11, 2012--.

Signed and Sealed this

Eleventh Day of June, 1996

Attest:

BRUCE LEHMAN

Attesting Officer     Commissioner of Patents and Trademarks